United States Patent
Gilad et al.

(10) Patent No.: US 11,877,990 B1
(45) Date of Patent: *Jan. 23, 2024

(54) AGMATINE COMPOSITIONS FOR TREATMENT OF OSTEOARTHRITIS

(71) Applicants: Gad M. Gilad, Las Vegas, NV (US); Varda H. Gilad, Las Vegas, NV (US)

(72) Inventors: Gad M. Gilad, Las Vegas, NV (US); Varda H. Gilad, Las Vegas, NV (US)

(*) Notice: Subject to any disclaimer, the term of this patent is extended or adjusted under 35 U.S.C. 154(b) by 0 days.

This patent is subject to a terminal disclaimer.

(21) Appl. No.: 18/118,686

(22) Filed: Mar. 7, 2023

Related U.S. Application Data

(63) Continuation of application No. 17/881,095, filed on Aug. 4, 2022, now Pat. No. 11,622,949.

(51) Int. Cl.
| | |
|---|---|
| *A61P 19/02* | (2006.01) |
| *A61K 31/155* | (2006.01) |
| *A61K 31/7076* | (2006.01) |
| *A61K 36/54* | (2006.01) |
| *A61K 38/39* | (2006.01) |
| *A61K 36/48* | (2006.01) |
| *A61K 31/10* | (2006.01) |
| *A61K 31/121* | (2006.01) |
| *A61K 31/167* | (2006.01) |
| *A61K 31/726* | (2006.01) |
| *A61K 31/7008* | (2006.01) |
| *A61K 36/9068* | (2006.01) |
| *A61K 31/455* | (2006.01) |
| *A61K 31/728* | (2006.01) |
| *A61K 36/324* | (2006.01) |

(52) U.S. Cl.
CPC ............ *A61K 31/155* (2013.01); *A61K 31/10* (2013.01); *A61K 31/121* (2013.01); *A61K 31/167* (2013.01); *A61K 31/455* (2013.01); *A61K 31/7008* (2013.01); *A61K 31/7076* (2013.01); *A61K 31/726* (2013.01); *A61K 31/728* (2013.01); *A61K 36/324* (2013.01); *A61K 36/48* (2013.01); *A61K 36/54* (2013.01); *A61K 36/9068* (2013.01); *A61K 38/39* (2013.01); *A61P 19/02* (2018.01)

(58) Field of Classification Search
CPC ....................................................... A61P 19/02
See application file for complete search history.

(56) References Cited

PUBLICATIONS

Taguchi et al, Agmatine for pain management in dogs with coxofemoral joint osteoarthritis: a pilot study. Frontiers in Veterinary Science (2018), vol. 5, No. December, pp. 311 (Year: 2018).*

* cited by examiner

*Primary Examiner* — Qiuwen Mi
(74) *Attorney, Agent, or Firm* — Trojan Law Offices

(57) ABSTRACT

Dietary supplements, nutraceutical compositions, medical foods, animal feeds, and pharmaceutical compositions for treating osteoarthritis and other osteo-articular conditions involving neuropathy and associated symptoms. A synergistic composition containing a high dose range of agmatine and acceptable salts thereof and in combination with other active ingredients having salutary effects in treating osteoarthritis and other osteo-articular conditions involving neuropathy and associated symptoms. The composition prepared with excipients and compatible carriers, including but not limited to, powders, tablets, capsules, controlled release carriers, lozenges and chewable preparations, liquid suspensions, suspensions in an edible supporting matrix or foodstuff and oral rehydration solution to facilitate consumption.

15 Claims, 2 Drawing Sheets

AGMATINE COMPOSITIONS FOR TREATMENT OF OSTEOARTHRITIS

CROSS-REFERENCE TO RELATED APPLICATION(S)

This Application is a continuation of pending U.S. patent application Ser. No. 17/881,095 filed on Aug. 4, 2022, the content of which is incorporated herein by reference in its entirety.

BACKGROUND

The present disclosure relates to compositions of matter in the field of dietary ingredients and nutraceuticals, dietary supplements, medical foods, foods, animal feeds and pharmaceutical compositions which incorporate them. More specifically, the disclosure is related to dietary supplement formulations which incorporate a high concentration of a neuroprotective ingredients beneficial in treating osteoarthritis. More specifically, the disclosure is related to agmatine and acceptable salts thereof for safe and long-term use in combination with other traditional dietary ingredients such as chondroitin, glucosamine, methyl-sulfonylmethane (MSM), hyaluronic acid, collagen, curcumin, S-aenosylmethionine, avocado/soybean unsaponifiables, boswellia serrata, ginger powder, polyphenols, niacinamide, and mixtures thereof. The disclosure is also directed to the treatment of osteoarthritis in animals by administering oral formulations consisting of the above ingredient combinations, among others.

Osteoarthritis

Osteoarthritis (OA) is the most common joint disorder. It is a progressive disease associated with variable pain intensity and loss of joint mobility which leads to a limited range of motion, and a reduced quality of life. OA is highly prevalent in aging populations, but also occurs in younger individuals, typically as a result of rigorous physical exertion. OA is a significant economic burden, and chronic pain associated with OA represents the main cause of disability for this condition.

A similar prevalence of OA occurs in companion animals, such as dogs, cats, horses, etc., with symptoms similar to symptoms seen in humans. The underlying pathology of OA is the result of an imbalance between tissue degradation and repair processes, resulting in continued cartilage degradation, loss of tissue components and abnormal bone production occurring in the joints.

The failure of known modalities for treating OA-related pain suggests a glaring unmet need for new OA treatments. OA-related pain is considered a nociceptive pain caused by sensitization of peripheral nerve terminals involving changes in joint nociceptors. Tissue pathology and inflammatory processes in the affected joints activate peripheral nociceptors causing peripheral sensitization and hyperexcitability of nociceptive neurons in the central nervous system as demonstrated by the relation of the magnitude of inflammation to the fluctuations in pain intensity.

However, nociception mechanisms are insufficient to explain two OA effects. One is the variability observed in pain manifestation between people as well as at different joints in the same person. Another is the often-observed treatment failure of anti-inflammatory drugs, including non-steroidal anti-inflammatory drugs (NSAIDs), cyclooxygenase (COX)-2-specific drugs (e.g., acetaminophen), and opiate analgesics. Increased evidence suggests that a neuropathic type of pain participates in generating OA-related pain. In contrast to inflammatory or nociceptive pain, which is caused by actual tissue damage or damaging stimuli, neuropathic pain is produced by direct injury or disease of the peripheral or the central nervous system.

Nutraceutical Supplements in Osteoarthritis Treatment

Conventional OA pain therapies such as NSAIDs, cyclooxygenase (COX)-2-specific drugs, and opiate analgesics not only have a low effectiveness for treating OA, but often cause severe adverse side effects including gastrointestinal problems, cardiovascular effects, and others. There is therefore a great deal of interest in nutraceutical supplements, which include a heterogeneous class of naturally occurring molecules having a great potential for reducing inflammation, oxidative stress, pain, and joint stiffness and improve cartilage formation in OA. The efficacy of different nutraceuticals varies, but their advantage is that they are generally well tolerated and safe.

Chondroitin sulfate, glucosamine, and methylsulfonylmethane (MSM) are the three most common dietary nutraceuticals in clinical practice for both human and animal OA patients. They are used in combinations consisting of various doses. They are precursors of cartilage formation and synovial fluid and are postulated to act as anti-inflammatory agents and antioxidants. However, there are some discrepancies in reported findings concerning their effectiveness for OA treatment.

Hyaluronic acid (HA) is a mucopolysaccharide, enriched particularly in synovial fluid with excellent viscoelasticity, high moisture retention capacity, thus acting as a lubricant, shock absorber and joint structure stabilizer. Additionally, HA may serve as a precursor for glucosamine. Intra-articular HA injections are considered the treatment of choice for improving symptoms in knee and hip OA. However, the multiple injections needed is a major drawback, and oral supplementation is therefore preferred. Several studies had demonstrated that oral HA is absorbed and distributed to the skin and joints. It is safe and can improve OA symptoms after a treatment of eight weeks or longer.

Collagen is a ubiquitous structural extracellular protein. Type II collagen is the major component (90-95% of total collagen content) of articular cartilage, forming the fibrils that give cartilage its tensile strength. The bioavailability of undenatured collagen is very low as it is physiologically unavailable for enteric absorption. Hydrolyzed collagen peptides can be absorbed by the gut. Oral administration of hydrolyzed collagen, used in dietary ingredient preparations at gram-range dosages, exerts anti-inflammatory effects and results in attenuation of OA-related pain and a reduction of the progression of articular cartilage degradation.

Recently, undenatured type II collagen supplementation in low milligram dosages had been found to reduce pain and improve other OA symptoms. Ingested undenatured collagen is postulated to exert its action via an 'oral tolerance' process. Interaction with the gut-associated immune system, results in forming specific reactive immune cells which enter the circulation and reach joints where they suppress cellular action involved in collagen breakdown.

Curcumin, the most significant curcuminoid extract of turmeric (Curcuma longa), is endowed with potent antioxidative and anti-inflammatory properties. Oral curcumin was found to be effective in improving mobility and reducing pain in people with OA, comparable to NSAID treatment.

Other plant extracts endowed with anti-inflammatory properties have been reported to reduce OA-related pain and mobility symptoms, and to significantly reduce the intake of NSAIDs or other pain killers. These include: avocado/soybean unsaponifiables, boswellia serrata, ginger powder (titrated in gingerols), and polyphenols from pomegranate (pycnogenol and anthocyanins), pine bark, and green tea (epigallocatechin 3-gallate).

Agmatine

Agmatine [(NH2(CH2)4NH2C(NH=)NH] is a ubiquitous naturally occurring molecule biosynthesized by decarboxylation of the amino acid arginine. Thus, it is also known as decarboxylated arginine. While agmatine is found in low concentrations in plant, fish, and meat derived foodstuffs, intestinal microbial production of agmatine is considered the main source for agmatine absorption into the body.

Agmatine Effects on Bodily Systems

Pharmacological treatment with agmatine exerts beneficial effects on various bodily functions, including mild antihypertensive, cardio-protective and nephro-protective effects. Of specific interest is substantial evidence demonstrating beneficial effects on the nervous system. These include neuroprotection, neuropathic pain-reducing effects, and anti-anxiety/anti-depressive effects. Enhanced glucose metabolism associated with increased insulin release, and reduced catecholamine release associated with a mild reduction in blood pressure and heart rate, are additional beneficial effects of agmatine that may contribute to its nervous system salutary effects.

Agmatine biosynthesis (by arginine decarboxylation) in the nervous system is normally very low, but is greatly increased in response to injury, thus further implicating agmatine in neuroprotection. While agmatine has long been known to stimulate the proliferation of thymocytes by modulating calcium action, it was found to be a cytotactic compound, preventing cell proliferation of various other cell types (including endothelial cells and astrocytes, as well as various cancer cells).

Agmatine Absorption, Distribution, and Metabolism

Animal studies demonstrated that agmatine is absorbed by the gastrointestinal tract and then rapidly (within minutes) distributed throughout the body, including the brain. In humans, ingested agmatine is readily absorbed and is eliminated unmetabolized by the kidneys with an apparent blood half-life of about two hours. Agmatine is principally metabolized into urea and putrescine, the diamine precursor of polyamines, which are generally essential for cell growth and viability and specifically for neuroprotection. In the periphery, rather than in the brain, agmatine can be oxidized and secreted by the kidneys. Agmatine can moderately increase glomerular filtration rate and natriuresis (increased sodium excretion), which may be desired or unwanted depending on a patient's health status.

Agmatine Mechanisms of Action

The mechanism of agmatine action is postulated to be multifunctional. Laboratory experiments indicate agmatine can modulate multiple molecular targets important for general cell viability (i.e., cytoprotection). These molecular targets include: (1) Modulation of several neurotransmitter receptors and receptor ionophores (e.g., nicotine, NMDA, imidazoline). (2) Blockage of key ionic channels (e.g., ATP-sensitive $K^+$ channels and voltage-gated $Ce^{++}$ channels). (3) Inhibitor of organic cation transporters (OCTs). (4) Inhibitor of nitric oxide (NO) synthesis, but modulator of overall NO production. (5) Precursor of polyamine synthesis and modulator of polyamine metabolism, molecules that play important roles in cell proliferation, and in cellular functions and repair mechanisms. (6) Inhibition of protein ADP-ribosylation and thus, interference with cell signaling. (7) Inhibition of matrix metalloproteases (MMPs) enzymes involved in extracellular matrix turnover and implicated in cell viability. (8) Inhibition of advanced glycation end (AGE)-product formation, an extracellular process involved in various systemic pathologies. Endowed with such exceptional modulatory properties, agmatine may exert its salutary effects by acting, perhaps simultaneously, like a molecular shotgun, at multiple molecular targets to maintain, protect and prevent tissue damage, thus promoting healthy bodily functions.

Utility of Agmatine for Osteoarthritis

The accrued evidence justifies the rational of using agmatine as a neuroprotective agent acting at multiple molecular targets to treat neuropathy and neuropathic pain, a recognized component of OA-related pain. The prior art is devoid of any references disclosing the use of agmatine itself and in combination with other known active nutraceutical ingredients as efficacious treatments for OA. Furthermore, it is now disclosed for the first time that agmatine, when administered together with other known active nutraceutical ingredients, can impart synergistic effects for improving OA symptoms.

It is therefore an object of the present disclosure to provide a method of administering effective, useful, and novel nutraceutical compositions that impart synergistic effects in improving OA symptoms incorporating effective agmatine dosage amounts, and acceptable nutraceutical salts thereof as a safe and long-term daily measure for improving OA symptoms. Another object of the disclosure is to provide an extended treatment method with these synergistic nutraceutical compositions, enabling dosage reductions of its ingredient components including agmatine.

SUMMARY

A method of enhancing osteoarthritis (OA) treatment in a human being (e.g., a patient) with OA symptoms, wherein the patient has a predetermined weight and is undergoing a concurrent conventional OA treatment is disclosed. A first dietary supplement having a first quantity of an agmatine salt is first provided and administered such that the first quantity of the agmatine salt is no more than 2,700 milligrams per 70 kilograms of the patient's weight. Administration of this first quantity is continued daily, and the patient is observed for an initial reduction in the patient's OA symptoms, as reported by the patient.

A second dietary supplement is provided, with the second dietary supplement including the ingredients of the first dietary supplement excepting a second quantity of the agmatine salt, wherein the second quantity is lower than the first quantity. The second dietary supplement is administered, with administration continued on a daily basis. The patient is then observed again to determine that a continued reduction in OA symptoms is reported by the patient. Administration of the second dietary supplement is continued on a daily basis, combined with the concurrent OA treatment, thereby providing ongoing relief of the OA symptoms.

In another implementation of the method, administering the second dietary supplement includes administering the second quantity at no more than 1,800 milligrams per 70 kilograms of the patient's weight. In yet another implementation of the method, administering the second dietary supplement includes administering the second quantity at no more than 1,350 milligrams per 70 kilograms of the patient's weight.

In one implementation the method includes providing, in the first dietary supplement, one or more additional ingredients selected from the group of chondroitin, glucosamine, methyl-sulfonylmethane (MSM), hyaluronic acid, collagen, curcumin, S-adenosylmethionine, avocado/soybean unsaponifiables, boswellia serrata, ginger, powder polyphenols, and niacinamide. This group is not intended to be mutually exclusive, and it is contemplated that one or more of the named compounds in the group may be selected according to preference.

In another implementation, the method includes providing an excipient in the first dietary supplement, the excipient configured to enable consumption of the first dietary supplement. The excipient in the first dietary supplement may be configured to enable or facilitate consuming the first dietary supplement and may include one or more additional ingredients selected from the group of chondroitin, glucosamine, methyl-sulfonylmethane (MSM), hyaluronic acid, collagen, curcumin, S-adenosylmethionine, avocado/soybean unsaponifiables, boswellia serrata, ginger, powder polyphenols, and niacinamide. The group of these additional ingredients is not meant to be mutually exclusive, and it is contemplated that one or more of the named compounds in the group may be selected according to preference.

In another implementation, the method may include incorporating the first dietary supplement into a processed food product. The food product may be selected from the group of cereals and fermented dairy products. In another implementation, the method may include incorporating the first dietary supplement into a beverage. The beverage may be selected from the group of tea, juice, water, and alcoholic beverages.

In a different implementation, a method of enhancing osteoarthritis (OA) treatment in an animal with OA symptoms is disclosed, wherein the animal has a predetermined weight and is undergoing a concurrent OA treatment. In this implementation a first dietary supplement is provided having a first quantity of an agmatine salt. The first dietary supplement is administered, such that the first quantity of the agmatine salt has a first milligram-to-animal weight ratio. Administration of the first dietary supplement with the first quantity is continued until an initial reduction in the OA symptoms is displayed by the animal and observed.

A second dietary supplement is provided, with the second dietary supplement including the ingredients of the first dietary supplement excepting a second quantity of the agmatine salt, the second quantity being lower than the first quantity. The second dietary supplement is administered, and the administration of the second dietary supplement continued on a daily basis. A continued reduction in the OA symptoms displayed by the animal is observed, and daily administration of the second dietary supplement combined with the concurrent OA treatment provides ongoing relief of the OA symptoms in the animal.

In one alternative implementation, the animal may be selected from the group of rats and mice, and the first milligram-to-animal weight ratio may be greater than 200 milligrams per kilogram of weight. In another alternative implementation, the animal may be selected from the group of rats and mice, and the first milligram-to-animal weight ratio may be less than 500 milligrams per kilogram of weight.

In a second alternative implementation, the animal may be a dog, and the first milligram-to-animal weight ratio may be greater than 20 milligrams per kilogram of weight. In another alternative implementation, the animal is a dog and the first milligram-to-animal weight ratio may be less than 80 milligrams per kilogram of weight.

In a third alternative implementation, the animal may be a horse and the first milligram-to-animal weight ratio may be greater than 10 milligrams per kilogram of weight. In another alternative implementation, the animal may be a horse and the first milligram-to-animal weight ratio may be less than 40 milligrams per kilogram of weight. In each of these implementations, the method may further include the step of providing a processed food that incorporates the first dietary supplement into an animal feed.

DESCRIPTION

Figure 1:
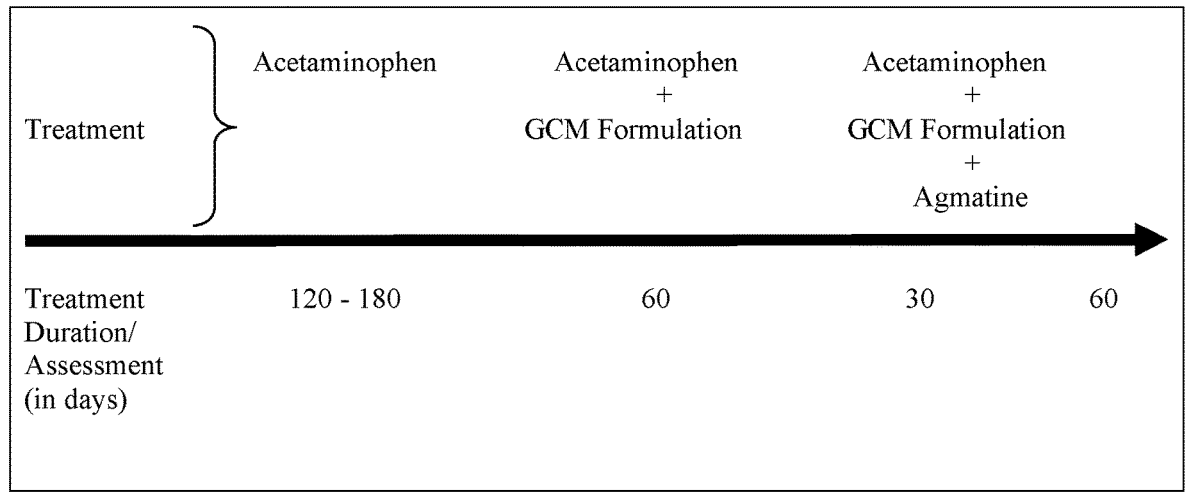
FIG. 1 illustrates a schematic presentation of a consecutive treatment regimen in accordance with an implementation of an agmatine treatment method.

The method will now be described more fully herein with reference to the accompanying drawings, in which implementations of the invention are shown. This disclosure may, however, be embodied in many different forms and should not be construed as limited to the implementations set forth herein. Rather, these implementations are provided so that this disclosure will be thorough and complete, and will fully convey the scope of the disclosure to those skilled in the art.

Unless otherwise defined, all terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The present disclosure provides a method for administering nutraceutical compositions for dietary supplements, medical foods, and processed foods and beverages, incorporating effective neuroprotective amounts of agmatine and nutraceutical acceptable salts thereof. These formulations, in combination with other dietary ingredients, have salutary effects on osteoarthritis and other osteoarticular conditions involving neuropathy and associated symptoms, such as neuropathic arthropathy and Lyme disease. Thus, the treatment fills a need not currently known.

A primary advantage of the present disclosure is to provide nutraceutical and dietary supplement compositions incorporating effective synergistic amounts of agmatine and nutraceutical acceptable salts thereof with salutary effects for osteoarthritis and any other osteoarticular conditions involving neuropathy and related symptoms in humans at a daily dose range of 0.5-3.5 grams, and in animals, depending on the family, at a daily dose range of 2-500 milligrams per kilograms body weight.

Another important advantage of the present disclosure is to provide dietary supplement formulations containing effective synergistic amount of agmatine and nutraceutical acceptable salts thereof in combination with other traditional dietary ingredients (including but not limited to Chondroitin, glucosamine, Methylsulfonylmethane (MSM), Hyaluronic acid, collagen, curcumin, S-Adenosylmethionine, avocado/soybean unsaponifiables, boswellia serrata, ginger powder, polyphenols, niacinamide) having salutary effects in osteoarthritis and any other osteoarticular conditions involving neuropathy and associated symptoms.

An additional advantage of the present invention is to provide the dietary supplement compositions described in (1) and (2) above in the form of powders, tablets, capsules, soft gelatin capsules, controlled release capsules and tablets, lozenges and chewable preparations, liquid suspensions, suspension in an edible supporting matrix or foodstuff and oral rehydration solutions, and to enable consumption of effective synergistic amounts of agmatine and other ingredients of the compositions.

A further advantage of the present invention is to provide nutraceutical compositions incorporating effective amounts agmatine and nutraceutical acceptable salts thereof as medical foods formulated to be consumed or administered enterally for dietary management of osteoarthritis and any other osteoarticular conditions involving neuropathy and related symptoms.

A further additional advantage of the present disclosure is to provide processed food compositions incorporating dietary ingredients and effective synergistic amounts of agmatine and nutraceutical acceptable salts thereof in accepted categories of functional foods and beverages. These include, but are not limited to, fermented dairy foods, and foods which are fortified with health promoting ingredients including, but not limited to: fibers, vitamins, minerals, fatty acids, amino acids, phytonutrients, and mixtures thereof.

Another advantage of the present disclosure is to provide an animal feed containing dietary compositions incorporating effective synergistic amounts agmatine and nutraceutical acceptable salts thereof for animals needing dietary management for OA and other osteoarticular conditions involving neuropathy and related symptoms. These and other advantages will become apparent as further described below in the various implementations of the disclosure. A person skilled in the art will realize that other embodiments of the invention are possible and that the details of the invention can be modified in a number of respects, all without departing from the inventive concept. Thus, the following description is to be regarded as illustrative in nature and not restrictive.

Two examples illustrate the advantages of the agmatine preparation and administration schedule disclosed herein. Although these two examples are illustrative of specific advantages of the present disclosure, the disclosure and implementations discussed herein are in no way limited to the given examples and other similar examples exist.

Agmatine Administration Case 1

Two study participants, each suffering from bilateral knee osteoarthritis, were consecutively self-treated as shown in the following Table 1: Treatment started with acetaminophen (as TYLENOL®, considered standard drug treatment) used as a rescue medication for the duration of their symptoms, 12 or 14 months as needed, followed by a 12-week treatment period of acetaminophen plus agmatine (taken as the G-AGMATINE® brand of agmatine sulfate).

The participants self-rated their OA symptoms according to the WOMAC (Western Ontario and McMaster Universities Osteoarthritis) Index and according to the Visual Analog (pain) Scale (VAS). They had bilateral symptoms of mild-to-moderate chronic, frequent knee pain typical of knee OA according to WOMAC, score range of >25 and <100. Table 1 presents a summary of the participants' characteristics and treatment assessment at the indicated follow-up times.

TABLE 1

| | Treatment Duration | | |
|---|---|---|---|
| | Acetaminophen | Acetaminophen plus Agmatine | |
| Rating Scale | 12-14 months | 6 weeks | 12 weeks |
| Participant #1: Male, 75 years old, with bilateral knee osteoarthritis for 14 months | | | |
| WOMAC (% Total Score) | 83.3 | 40.6 | 32.3 |
| VAS Score | 6.0 | 3.0 | 2.0 |
| Participant #2: Male, 71 years old, with bilateral knee osteoarthritis for 12 months | | | |
| WOMAC (% Total Score) | 85.4 | 44.8 | 34.4 |
| VAS Score | 6.5 | 3.5 | 2.5 |

For the entire acetaminophen-only treatment, the dosage was 500 milligrams per caplet, and the frequency was two caplets every six hours, as needed (i.e., 1000 mg per six-hour period). For the acetaminophen plus agmatine regimen, the participants' initial dosage of acetaminophen was 500 milligrams per caplet with an initial dosage of agmatine of 450 milligrams per capsule. While the frequency of acetaminophen dosage for both participants remained two caplets every six hours, the frequency of the agmatine capsules was six capsules daily (i.e., 2,700 mg per day).

Over the course of the acetaminophen plus agmatine regimen, the participants gradually reduced their acetaminophen dosing. Participant 1 eliminated acetaminophen after six weeks, and participant 2 eliminated acetaminophen after eight weeks of treatment. Thereafter, the participants were taking only agmatine and reduced the quantity of agmatine by one third (i.e., a regimen of 1,800 mg per day).

These findings illustrate for the first time that treatment with agmatine can exert dramatic improvement in OA symptoms, indicating an unexpected synergistic effect of agmatine when taken with acetaminophen. This beneficial effect of agmatine treatment leads to a reduction in the need for, or altogether cessation of acetaminophen treatment, which in turn reduces or eliminates the serious side effects associated with acetaminophen medication.

Agmatine Administration Case 2

In a second study, four participants had bilateral symptoms of mild-to-moderate chronic, frequent knee pain typical of knee osteoarthritis according to a WOMAC Index score range of >25 and <100. They are compared in Table 2. Participants began taking acetaminophen (as TYLENOL®) as needed over the course of the symptom duration:

TABLE 2

| | Participant | | | |
|---|---|---|---|---|
| Characteristic | #1 | #2 | #3 | #4 |
| Gender | Male | Female | Male | Male |
| Age (years) | 76 | 69 | 74 | 74 |
| Knee Osteoarthritis | Bilateral | Bilateral | Bilateral | Bilateral |
| Symptom Duration (days) | 180 | 168 | 159 | 120 |

Referring to FIG. 1, the four participants self-treated consecutively as follows: starting with Acetaminophen (as TYLENOL®, considered a standard drug treatment) used as a rescue medication for the duration of their symptoms for 4 to 6 months, followed by a sixty-day treatment period with acetaminophen plus a GCM formulation (i.e., glucosamine HCl, chondroitin sulfate, and methylsulfonylmethane (MSM)). The GCM formulation was followed by sixty-day period using a combination comprising acetaminophen, the GCM formulation, and agmatine (taken as the G-AGMATINE® brand of agmatine sulfate).

The treatment dosages and frequencies were as follows: During the acetaminophen (as TYLENOL®) alone regimen, a dosage of 500 milligrams per caplet was taken at a frequency of two caplets every six hours, as needed. During the acetaminophen/GCM formulation regimen, glucosamine HCl was taken at 2,000 milligrams per day, chondroitin sulfate was taken at 1,200 milligrams per day, and methylsulfonylmethane (MSM) was taken at 500 milligrams per day. These were taken in a liquid form of two tablespoons once a day. During the acetaminophen/GCM formulation/agmatine regimen (taken as the G-AGMATINE® brand of agmatine sulfate) a dosage of 450 milligrams per capsule was taken at a frequency of six capsules daily (2,700 mg per day).

Figure 2:
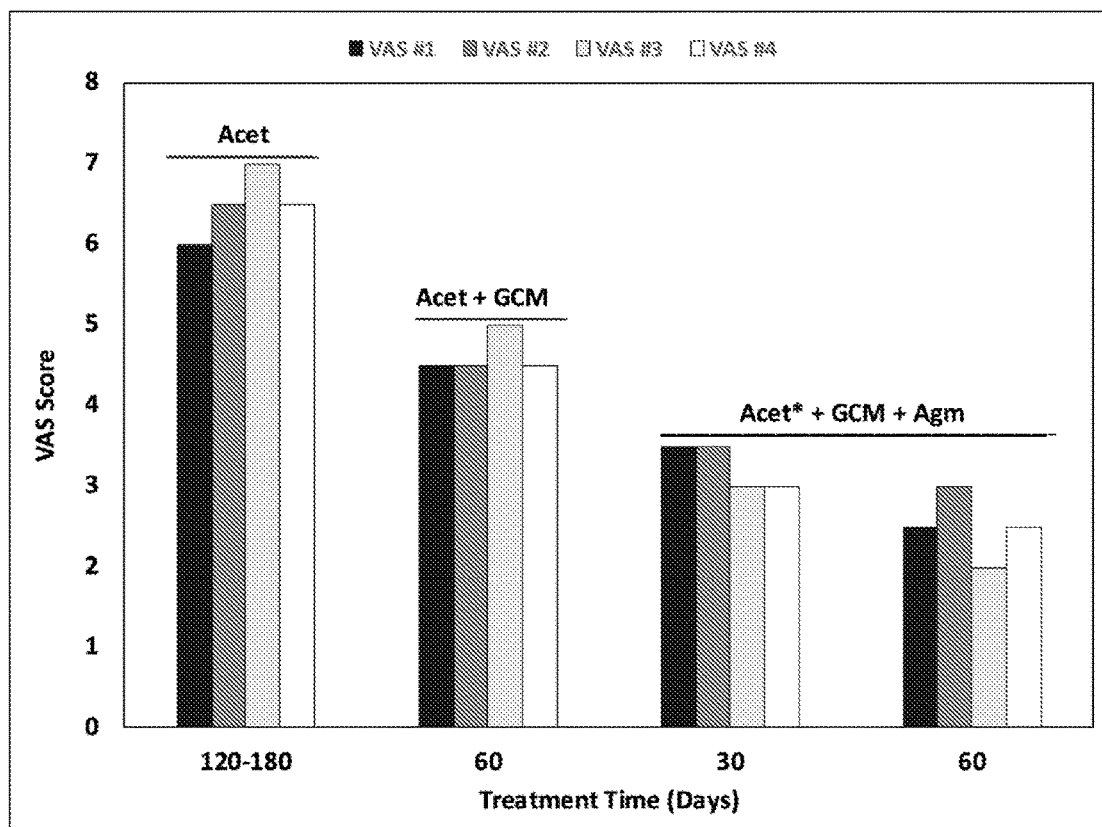
FIG. 2 illustrates various changes in the Visual Analog (pain) Scale (VAS), shown at specified time intervals after commencement of the consecutive treatment regimen.
Figure 3:
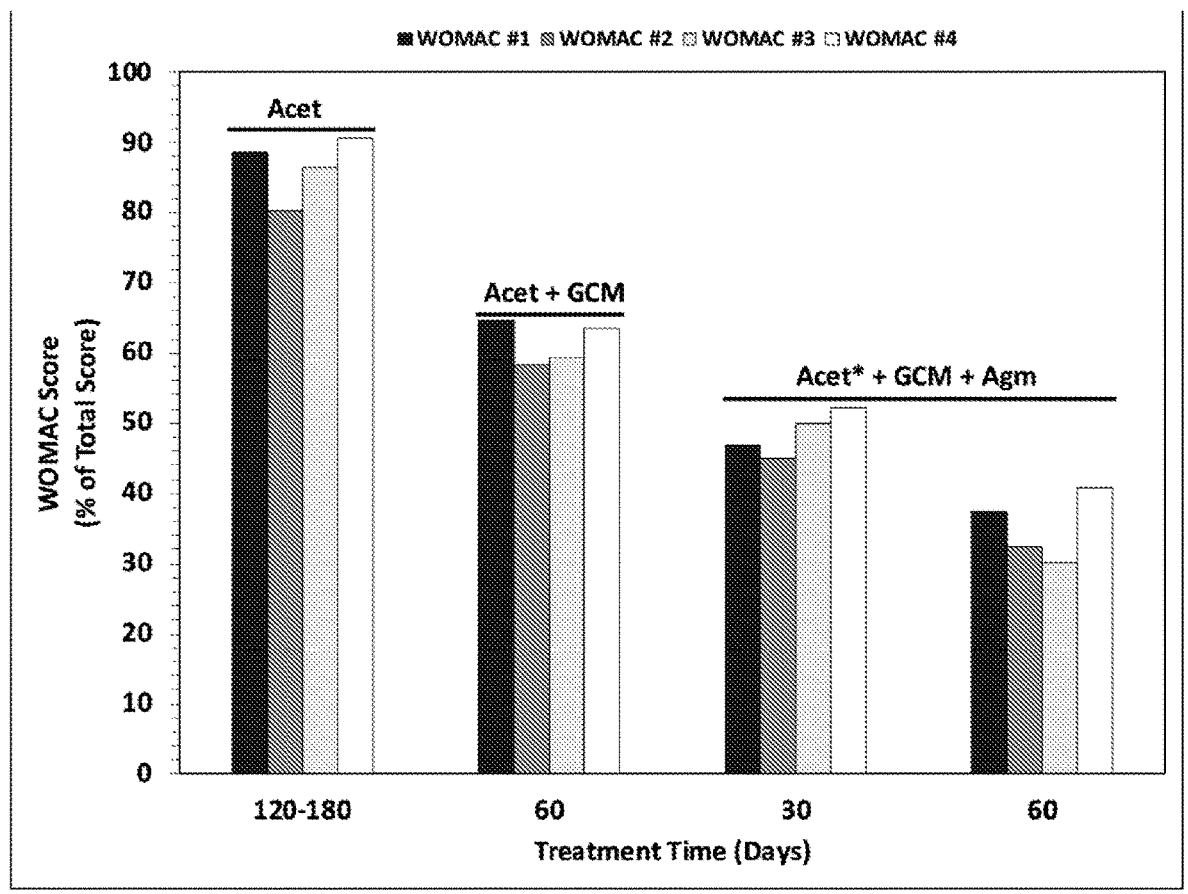
FIG. 3 illustrates various changes in the WOMAC (Western Ontario and McMaster Universities Osteoarthritis) pain index, shown at specified time intervals after commencement of the consecutive treatment regimen.

Referring to FIGS. 1-3, the participants self-rated their symptoms at the end of each treatment period as shown in FIG. 1, according to the VAS pain scale, as shown in FIG. 2, and according to the WOMAC Index ratings as shown in FIG. 3. Treatments were initiated at the beginning, and assessments were made at the last day of each period reflected in FIG. 1.

Referring to FIG. 2, changes in VAS pain scores are shown at the specified time intervals, after the initiation of each regimen of acetaminophen (labeled "acet" in the figure), acetaminophen/GCM formulation, and acetaminophen/GCM formulation/agmatine treatments. The four participants' scores are represented by bar graphs in different shades of gray. Referring to the acetaminophen/GCM formulation/agmatine treatment specifically (identified by an asterisk in the figure), the participants gradually reduced acetaminophen dosing, and ceased taking it after about forty days of treatment. After forty days, participants were able to reduce their daily dosage to a maintenance regimen of only agmatine and the GCM formulation by one third and one half, respectively.

Referring to FIG. 3, changes in the WOMAC ratings are shown, expressed as a percentage of total scores, at the specified time intervals after initiation of each of the acetaminophen (labeled "acet in the figure), acetaminophen and GCM formulation, and the combination acetaminophen/GCM formulation/agmatine treatment regimens. The four participants' scores are represented by bar graphs in different shades of gray. Referring to the acetaminophen/GCM formulation/agmatine treatment specifically (identified by an asterisk in the figure), the participants gradually reduced acetaminophen dosing and ceased taking it after about forty days of treatment. After forty days of the combination treatment, participants were able to lower their daily dosage of agmatine and the GCM formulation by one third and one half, respectively.

These findings illustrate that, for the first time, an unexpected synergistic effect of agmatine on improving OA symptoms when taken with acetaminophen, and when taken with a combination acetaminophen/GCM Formulation. This unexpected beneficial effect of agmatine treatment leads to a reduction in the need for (or altogether cessation of) acetaminophen treatment, which in turn reduces or eliminates the serious side effects associated with acetaminophen-based medications. In addition, the treatment combination of agmatine and the GCM formulation leads to a reduction in the dose quantities required to achieve effective OA symptom improvements, which in turn results in patient cost savings.

Moreover, the findings shown in cases 1 and 2, discussed above, indicate that when taken concomitantly with other OA treatments, agmatine treatment enables patients to lower their treatment regimens while achieving similar pain relief effectiveness.

In an alternative implementation of the disclosed method, a final product treatment composition may be delivered in hard-shell, gelatin or in HPMC (HydroxyPropylMethylCellulose) capsules prepared using the following ingredients: A mixture containing 450 milligrams (per capsule) of an agmatine sulfate and 6.5 milligrams (per capsule) of an undenatured type II collagen is filled into hard-shell capsules (preferably size 0 capsules), without the use of excipients. Proportionally larger quantities may be filled into larger size capsules.

In another alternative implementation of the disclosed method, a final product treatment composition consists of a mixture containing the following ingredients per dose: 1,350 milligrams of an agmatine sulfate, 800 milligrams of glucosamine HCl, 600 milligrams of chondroitin sulfate, and 250 milligrams of methylsulfonylmethane (MSM). The powder mixture, 3,000 milligrams in total, is filled into plastic sachets for storage, and the contents are dissolved in a quantity of a preferred beverage prior to use.

In yet another alternative implementation of the disclosed method, treatment compositions comprising agmatine sulfate and one or more nutraceutical ingredients is based on predicted results as reported in the literature and discussed in the Background section above as suitable for nutraceutical supplement products. Without limitation, the following compositions of the present invention may include: A composition of agmatine sulfate dosed at 2,700 milligrams per day with a hydrolyzed type II collagen dosed at 5,000 milligrams per day. A composition of agmatine sulfate dosed at 2,700 milligrams per day with a hyaluronic acid dosed at 240 milligrams per day. A composition of agmatine sulfate dosed at 2,700 milligrams per day with curcumin dosed at 2,000 milligrams per day. And a composition of agmatine sulfate dosed at 2,700 milligrams per day, with boswellia serrata dosed at 100 milligrams per day, and avocado/soybean unsaponifiables dosed at 200 milligrams per day.

Various other exemplary implementations of compositions and modifications or adaptations thereof can be devised by a person skilled in the art after reading the various implementations discussed herein without departing from the spirit and scope of this disclosure. All such modifications and adaptations are therefore included within the scope of this disclosure.

It will be appreciated by those skilled in the art that the present disclosure makes available novel and useful nutraceutical compositions containing agmatine and nutraceutical acceptable salts thereof, which have OA salutary effects in several administration forms. Also, it will be understood by those with knowledge in the dietary supplement, nutraceutical, and pharmaceutical art, that many implementations of this disclosure may be made without departing from the spirit and scope of the disclosure, and the disclosure is not to be construed as limited, as it embraces all equivalents herein.

What is claimed is:

1. A method of enhancing a conventional osteoarthritis treatment in a human patient by undergoing a concurrent method of osteoarthritis treatment, the concurrent method comprising the steps of:

daily administration of a first dietary supplement having a first quantity of an agmatine salt followed by daily administration of a second dietary supplement having a second quantity of the agmatine salt, the second quantity of the agmatine salt is lower than the first quantity of the agmatine salt;

whereby the daily administration of the first dietary supplement followed by the daily administration of the second dietary supplement enhances the conventional osteoarthritis treatment in the human patient.

2. The method of claim 1, wherein the human patient having a certain weight, and wherein the daily administration of the first dietary supplement comprising administering the first quantity of the agmatine salt at no more than 2,700 milligrams per 70 kilograms of the human patient's weight.

3. The method of claim 1, wherein the human patient having a certain weight, and wherein the daily administration of the second dietary supplement comprises administering the second quantity of the agmatine salt at no more than 1,800 milligrams per 70 kilograms of the human patient's weight.

4. The method of claim 1, wherein the human patient having a certain weight, and wherein the daily administration of the second dietary supplement comprises administering the second quantity of the agmatine salt at no more than 1,350 milligrams per 70 kilograms of the human patient's weight.

5. The method of claim 1 wherein:
the first dietary supplement is incorporated into a medical food;
the first dietary supplement is incorporated into a processed food product selected from the group of cereals and fermented dairy products; or
the first dietary supplement is incorporated into a beverage selected from the group consisting of tea, juice, water, and alcoholic beverages.

6. The method of claim 1, wherein the agmatine salt is agmatine sulfate.

7. A method of enhancing a conventional non-steroidal anti-inflammatory drug (NSAID) treatment of osteoarthritis in humans, the method comprising the steps of:
daily administration of a dietary supplement;
the dietary supplement comprising a quantity of an agmatine salt and one or more additional ingredients selected from the group consisting of chondroitin, glucosamine, methyl-sulfonylmethane (MSM), hyaluronic acid, collagen, curcumin, S-adenosylmethionine, avocado/soybean unsaponifiables, boswellia serrata, ginger, powder polyphenols, and niacinamide;
whereby the daily administration of the dietary supplement enhances the conventional NSAID treatment of osteoarthritis.

8. The method of claim 7 further comprising the step of providing an excipient in the dietary supplement, the excipient configured to enable consumption of the dietary supplement.

9. A method of enhancing a conventional species specific osteoarthritis treatment in an animal by undergoing a concurrent method of osteoarthritis treatment, the concurrent method comprising the steps of:
daily administration of a first dietary supplement having a first quantity of an agmatine salt to the animal followed by daily administration of a second dietary supplement having a second quantity of the agmatine salt, the second quantity of the agmatine salt is lower than the first quantity of the agmatine salt;
whereby the daily administration of the first dietary supplement followed by the daily administration of the second dietary supplement enhances the conventional osteoarthritis treatment in the animal.

10. The method of claim 9, wherein the animal having a weight, the animal is selected from the group consisting of rats and mice, the first quantity of the agmatine salt having a milligram-to-animal weight ratio, and the milligram-to-animal weight ratio is greater than 200 milligrams per kilogram of weight.

11. The method of claim 9, wherein the animal having a weight, the animal is selected from the group consisting of rats and mice, the first quantity of the agmatine salt having a milligram-to-animal weight ratio, and the milligram-to-animal weight ratio is less than 500 milligrams per kilogram of weight.

12. The method of claim 9, wherein the animal having a weight, the animal is a dog, the first quantity of the agmatine salt having a milligram-to-animal weight ratio, and the milligram-to-animal weight ratio is greater than 20 milligrams per kilogram of weight.

13. The method of claim 9, wherein the animal having a weight, the animal is a dog, the first quantity of the agmatine salt having a milligram-to-animal weight ratio, and the milligram-to-animal weight ratio is less than 80 milligrams per kilogram of weight.

14. The method of claim 9, wherein the animal having a weight, the animal is a horse, the first quantity of the agmatine salt having a milligram-to-animal weight ratio, and the milligram-to-animal weight ratio is greater than 10 milligrams per kilogram of weight.

15. The method of claim 9, wherein the animal having a weight, the animal is a horse, the first quantity of the agmatine salt having a milligram-to-animal weight ratio, and the milligram-to-animal weight ratio is less than 40 milligrams per kilogram of weight.

* * * * *